US011109169B2

(12) United States Patent
Gozzelino

(10) Patent No.: US 11,109,169 B2
(45) Date of Patent: Aug. 31, 2021

(54) METHOD FOR SELECTING AND ADJUSTING IN A CUSTOMIZED MANNER A HEARING AID

(71) Applicant: AMPLIFON S.P.A., Milan (IT)

(72) Inventor: Gian Carlo Gozzelino, Milan (IT)

(73) Assignee: Amplifon S.p.a., Milan (IT)

( * ) Notice: Subject to any disclaimer, the term of this patent is extended or adjusted under 35 U.S.C. 154(b) by 331 days.

(21) Appl. No.: 16/323,495

(22) PCT Filed: Aug. 7, 2017

(86) PCT No.: PCT/IB2017/054829
§ 371 (c)(1),
(2) Date: Feb. 5, 2019

(87) PCT Pub. No.: WO2018/025250
PCT Pub. Date: Feb. 8, 2018

(65) Prior Publication Data
US 2021/0092537 A1  Mar. 25, 2021

(30) Foreign Application Priority Data
Aug. 5, 2016  (IT) .......................... 102016000083180

(51) Int. Cl.
 *H04R 25/00* (2006.01)
 *A61B 5/12* (2006.01)
(52) U.S. Cl.
 CPC ............. *H04R 25/70* (2013.01); *A61B 5/123* (2013.01)
(58) Field of Classification Search
 CPC ........ H04R 25/30; H04R 25/50; H04R 25/70; H04R 25/305; H04R 2225/41; H04R 2225/43
 See application file for complete search history.

(56) References Cited

U.S. PATENT DOCUMENTS
2013/0023787 A1  1/2013  Dowd

FOREIGN PATENT DOCUMENTS
WO  0197564 A2  12/2001

OTHER PUBLICATIONS

International Search Report and Written Opinion for related application PCT/IB2017/054829, dated Nov. 6, 2017; 3 pages.
(Continued)

*Primary Examiner* — Matthew A Eason
(74) *Attorney, Agent, or Firm* — Loza & Loza, LLP

(57) ABSTRACT

Method for selecting and adjusting in a customised manner a hearing aid comprising the following steps: A. receiving (100) indications on one or more needs of a patient; B. receiving (200) indications from the patient concerning his/her perception of his/her own hearing with respect to listening situations by assigning a respective value on a first value scale; C. performing (300) an audiometric PTA test on the patient, wherein the patient wears a headset and hearing is not assisted by any hearing aid; D. performing (400) an audiometric ANL test on the patient; E. in the case where the resulting value of the audiometric PTA test is not larger than 80 dB, performing (500) an audiometric SPIN test on the patient; F. in the case where the resulting value of the audiometric PTA test is larger than 80 dB, or in the case where the resulting value of the audiometric PTA test is not larger than 80 dB and the resulting value of the SPIN test is larger than 6, performing (600) an audiometric SPIQ test on the patient, wherein the patient wears a headset; G. displaying (700) the resulting values of the audiometric tests performed in steps C, D, E and/or F on a same second value scale; H. selecting (800) one or more available hearing aids, J. automatically determining (900) a related adjustment of operating parameters of the respective signal processing unit to allow meeting the needs determined in step A.

18 Claims, 5 Drawing Sheets

(56) References Cited

OTHER PUBLICATIONS

Hemanth Narayan Shetty et al.; "Acceptable noise level as a deciding factor for prescribing hearing aids for older adults with cochlear hearing loss—A scoping review"; Journal of Otology, vol. 10, No. 3, Sep. 1, 2015; pp. 93-98.

Robyn M Cox; "Hearing Aids and Aural Rehabilitation—A Structured Approach to Hearing Aid Selection"; Sep. 1, 1985, Retrieved from the Internet: http://www.harlmemphis.org/files/5914/0269/2785/Structured_approach_to_hearing_aid_selection.pdf, May 2, 2017.

Carole E. Johnson et al.; "A Holistic Model for Matching High-tech Hearing Aid Features to Elderly Patients", American Journal of Audiology, vol. 9, No. 2; Dec. 1, 2000, p. 112.

College of Audiologist and Speech-Language Pathologist of Ontario; "Practice Standards and Guidelines for Hearing Assessment of Adults by Audiologists"; Apr. 1, 2014, Retrieved from the Internet, http://www.caslpo.com/sites/default/uploads/files/PSG_EN_Hearing_Assessment_of_Adults_by_Audiologists.pdf, retrieved on May 3, 2017.

METHOD FOR SELECTING AND ADJUSTING IN A CUSTOMIZED MANNER A HEARING AID

The present invention refers to a method for selecting and adjusting in a customised manner a hearing aid, more particularly a method for selecting through proper measurements the most suitable hearing aid for a specific patient and for adapting it in a customised manner, that allows in a simple, reliable, efficient and inexpensive way to select the most suitable hearing aid model (i.e. provided with the technical functionalities necessary for the customer's hearing needs) and to adjust its settings of electronic signal processing in a customised manner for the patient. This allows the patient to obtain concrete results in any experienced listening situation: in fact, the method, besides checking the starting hearing situation with audiometric tests, converts data in objective indications related to the choice and adaptation of the aid, uses a preferably univocal measurement scale allowing to compare the results of the need collection and of the audiometric tests, also comparing the hearing in pre- and post-application of the hearing aid. This allows to obtain a very high standard of a process currently depending on the habits of the individual audiology technician, drastically reducing the need for adjustments after the first delivery of the hearing aid to the patient.

It is known that to correct hearing impairments, patients wear (analog or digital) electronic hearing aids. Generally, these are provided with an (analog or digital) signal processing unit that processes an electrical signal coming from a microphone system capable to simulate several functionalities by focusing on certain sounds in relation to their provenance with respect to the microphone; the thus processed electrical signal is then played in the ear canal by a miniature loudspeaker. In particular, the electrical signal processing carried out by a hearing aid must be adjusted in a customised manner to correct hearing impairments of each specific patient, and this is carried out by setting some operating parameters of the signal processing unit.

At the present state of the art, a single instrumental test is performed on the customer asserting a hearing loss on the basis of the results of which the audiologist selects the hearing aid model to apply. Also, most operating parameters of a hearing aid are initially present to default values by the aid manufacturer on the basis of statistical averages. After having discussed with the patient on the quality perceived by the latter after a first time period of aid use, the audiologist may intervene to modify the setting of the operating parameters upon indication of the same patient, substantially proceeding to the adjustment of the hearing aid in an empirical way through subsequent attempts.

However, this procedure of hearing aid adjustment, substantially based on the patient's subjective perception, hinders a complete and accurate customisation of the hearing aid.

With regard to the adjustment of the operating parameters of the hearing aid, the solutions developed in the prior art (adjustment software programs) allow a greater ease of execution of the adjustment procedure that, however, is still based on the patient's subjective perception after a first time period of aid use. Some of such solutions, also remotely operating, are disclosed in documents U.S. Pat. No. 5,303,306A, WO0154458A2, WO2010144135A1 and EP2549397A1.

Thus, it is an object of the present invention to allow in a simple, reliable, efficient and inexpensive way to select the hearing most suitable for the patient and to adjust the settings of the electronic signal processing performed by a hearing aid in a customised manner for the patient, drastically reducing or even eliminating the need for adjustments after the first delivery of the hearing aid to the patient.

It is specific subject matter of the present invention a method for selecting and adjusting in a customised manner a hearing aid, including a signal processing unit configured to process an electrical signal coming from one or more microphones and to play a resulting processed electrical signal in an ear canal of a patient through a miniature loudspeaker, wherein processing of the electrical signal is adjustable by means of settings of one or more operating parameters of the signal processing unit, wherein the method comprises the following steps:

A. receiving indications on one or more needs of a patient;
B. receiving indications from the patient concerning his/her perception of his/her own hearing with respect to one or more listening situations by assigning a respective value on a first value scale having a lower limit and an upper limit;
C. performing a Pure Tone Audiometry audiometric test, also known as PTA test, on the patient, wherein the patient wears a headset and hearing is not assisted by any hearing aid;
D. performing an Acceptable Noise Level audiometric test, also known as ANL test, on the patient;
E. in the case where the resulting value of the audiometric PTA test is not larger than 80 dB, performing a Speech in Noise test, also known as SPIN test, on the patient;
F. in the case where the resulting value of the audiometric PTA test is larger than 80 dB, or in the case where the resulting value of the audiometric PTA test is not larger than 80 dB and the resulting value of the SPIN test is larger than 6, performing a Speech in Quiet test, also known as SPIQ test, on the patient, wherein the patient wears a headset;
G. displaying the resulting values of the audiometric tests performed in steps C, D, E and/or F on a same second value scale;
H. on the basis of said one or more needs of the patient on which indications have been received in step A and on the basis of the resulting values of the audiometric tests performed in steps C, D, E and/or F, selecting one or more available hearing aids,
J. for each one of said one or more available hearing aids selected in step H, on the basis of said one or more needs of the patient on which indications have been received in step A and on the basis of the resulting values of the audiometric tests performed in steps C, D, E and/or F, automatically determining a related adjustment of operating parameters of the respective signal processing unit to allow meeting the needs determined in step A.

According to another aspect of the invention, in step D and step E the patient may wear a headset when the ANL and SPIN tests, respectively, are performed outdoors, while the ANL and SPIN tests, respectively, may be performed in free field when indoors.

According to a further aspect of the invention, the ANL test of step D may comprise one or more measurements, optionally five measurements.

According to an additional aspect of the invention, said first value scale may be a scale of integers from 0 to 10, wherein 0 corresponds to a perception of total hearing loss and 10 corresponds to a perception of absence of hearing loss.

According to another aspect of the invention, said second value scale may be identical to said first value scale.

According to a further aspect of the invention, said operating parameters may concern functions of electronic processing of the acoustic signal comprising or consisting of:
- a management of amplification level;
- with reference to an amplitude compression, a management of level of intervention of compression and a compression ratio;
- a management of a frequency compression and of a related frequency shift;
- a microphone setting mode for selecting one or both of two microphone inputs corresponding to the front microphone and the rear microphone and for selecting a frequency band of the signals acquired by the selected microphone or microphones;
- a management of an anti-feedback system configured to selectively attenuate frequencies at which a Larsen effect occurs;
- a Voice and Noise management (S/N Manager);
- a management of transient and sudden sounds; and
- a management of reverberant listening environments.

According to an additional aspect of the invention, said adjustment of operating parameters in step J may comprise transforming the results of the ANL, SPIN and/or SPIQ tests of steps D, and E and/or F, respectively, in one of the following three settings:
- natural fitting that substantially entails no processing of the acoustic signal, wherein optionally the S/N manager parameters are set to a minimum for limiting its operation as much as possible and microphone management can simulate a natural listening of a normal hearing ear substantially without introducing changes upon variation of sound environment;
- from natural to moderately controlled fitting that entails adjustments of specific operating parameters for at least one desired listening situation not larger than respective first modification thresholds, wherein optionally the S/N manager parameters are set at a medium level to intervene only if a noise level gets higher than a respective noise threshold and the microphone management can simulate a natural listening of a normal hearing ear, and more optionally it can carry out one or more corrections in case of listening in sound environments with several sound sources not manageable by the S/N manager; and
- from moderately controlled to significantly controlled fitting that entails adjustments of specific operating parameters for at least one desired listening situation larger than the respective first modification thresholds, wherein optionally the S/N manager parameters are set at a high level to protect the patient from noises which he/she could perceive as troublesome and the microphone management can vary focusing upon variation of listening situation.

According to another aspect of the invention, said one or more needs on which indications are received in step A may be selected from the group comprising: better hearing in quiet environment from close distance; better understanding in open environment from close distance; better hearing distant sounds or voices; better comfort in daily listening; better understanding a television; better understanding in a small group of people with no other sounds; automatic adaptation to different listening situations; wireless connectivity; better perceiving a sound provenance; better understanding in environment with many people talking and other sounds; good listening comfort in noisy situations; better understanding a person speaking in wide environment or at a distance; better quality of listening to music and voice even in presence of noise; better understanding outdoors in presence of noise or wind and/or for sports activities.

According to a further aspect of the invention, said one or more listening situations with respect to which indications from the patient concerning his/her perception of his/her own hearing are received in step A may be six different hearing situations comprising: hearing soft sounds; understanding words in quiet; understanding words in noise; situation of tolerable noise; ability to locate sounds; and ability of concentration during a dialogue.

According to an additional aspect of the invention, the method may further comprise an additional checking step that includes performing a SPIN test, if step E has been performed, and performing a SPIQ test, if step F has been performed, with the hearing aid adjusted according to the related adjustment of operating parameters of the respective signal processing unit determined in step J.

According to another aspect of the invention, in the SPIN test of the additional checking step patient's hearing may be aided by a former hearing aid.

According to a further aspect of the invention, said additional checking step may further include performing a balancing test within a structure equipped with free field.

According to an additional aspect of the invention, the method steps may be performed by means of a software application.

According to another aspect of the invention, step G may display a comparison of hearing abilities perceived by the patient with objective hearing abilities detected in the audiometric tests performed in steps C, D, E and/or F.

According to a further aspect of the invention, step H may display benefits resulting from different hearing aids available for the patient with reference to said one or more needs on which indications have been received in step A.

It is also specific subject matter of the present invention a set of one or more computer programs comprising instructions which, when executed by one or more processing units, cause said one or more processing units to perform the method for selecting and adjusting in a customised manner a hearing aid described above.

It is further specific subject matter of the present invention a set of one or more computer readable memory media, storing the set of one or more computer programs just described.

In other words, the method for selecting and adjusting in a customised manner a hearing aid according to the invention:
- determines and selects the hearing aid most suitable for the patient on the basis of the indications obtained from the fusion of collected (and advantageously recorded) data by means of a precise series of instrumental audiometric tests with those resulting from a detailed mapping of the hearing needs expressed by the patient;
- adjusts the settings of the electronic signal processing performed by the hearing aid in a customised manner for the patient, drastically reducing or even eliminating the need for adjustments after the first delivery of the hearing aid to the patient; and
- measures the results and compares them with collected (and advantageously recorded) data to refine the adjustment.

The advantages offered by the method for selecting and adjusting in a customised manner a hearing aid according to the invention are numerous.

In fact, an audiologist is capable to adjust the operating parameters of the hearing aid, i.e. the settings of the electronic signal processing performed by the hearing aid, advantageously through the fitting software programs of the hearing aid manufacturers, so as to completely and accurately customise them on the basis of the patient's needs and his/her objective hearing abilities (besides the specific hearing aid selected by the patient with the help of an audiologist) before the first use of the hearing aid by the patient. In particular, the inventors have ascertained that in almost all the carried out experimentations the adjustment set through the method according to the invention has been fully satisfactory without any need for successive modifications of the operating parameters of the hearing aid.

Moreover, the preferred embodiment of the method according to the invention makes use of a software application allowing to display in a convenient way for the patient the results obtainable with the selected hearing aid, in particular showing a comparison between perceived hearing abilities (i.e. the ones that the patient deems to have in different listening situations) and objective hearing abilities (i.e. the ones resulting from audiometric tests performed with the method according to the invention) both in the situation preceding the application of the hearing aid and in the situation when the hearing aid is worn, highlighting the benefit achieved through prosthesisation.

The present invention will be now described, by way of illustration and not by way of limitation, according to its preferred embodiments, by particularly referring to the Figures of the annexed drawings, in which.

Figure 1:
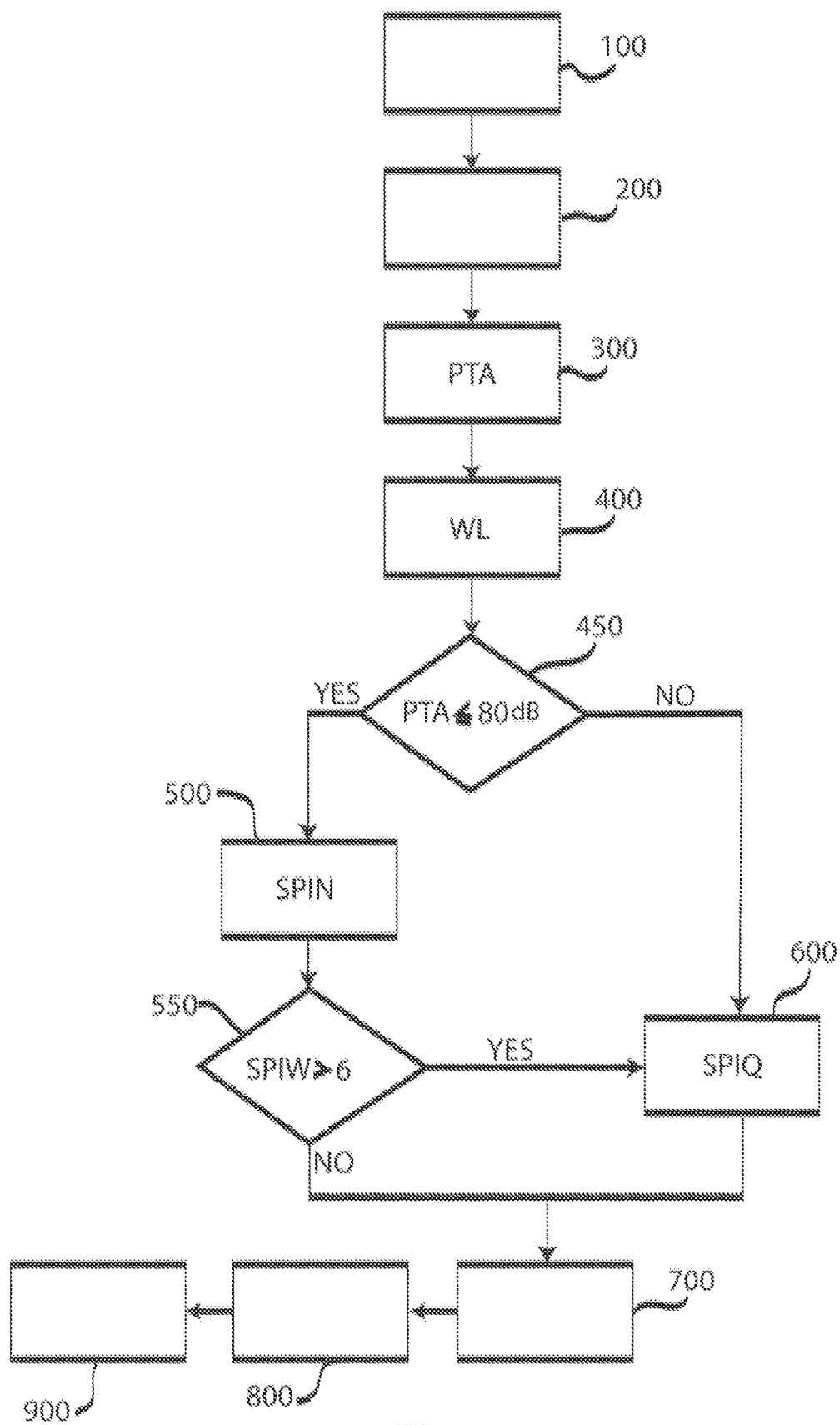
FIG. 1 shows a schematic block diagram of a preferred embodiment of the method for selecting and adjusting in a customised manner a hearing aid according to the invention.

With reference to FIG. 1, it may be observed that the preferred embodiment of the method for selecting and adjusting in a customised manner a hearing aid according to the invention comprises a first step 100 wherein indications on one or more needs of the patient and, optionally, on one or more possible needs of patient's family members are received. Such first step is advantageously carried out by an audiologist by recording data, through a software application, collected in a first meeting with the patient to determine and select the hearing aid, within a group of available hearing aids, that is the most suitable for the patient in terms of costs and general performance. Advantageously, data recording comprises the faithful memorisation of the words of the patient (and possibly of the family members).

By way of example, and not by way of limitation, such needs may be selected from the group comprising: better hearing in quiet environment from close distance; better understanding in open environment from close distance; better hearing distant sounds or voices; better hearing comfort in daily life; better understanding the television; better understanding in a small group of people with no other sounds; automatic adaptation to different listening situations; wireless connectivity; better perceiving the sound provenance; better understanding in environment with many people talking and other sounds; good listening comfort in noisy situations; better understanding a person speaking in wide environment or at a distance; better quality of listening to music and voice even in presence of noise; better understanding outdoors in presence of noise or wind, or for sports activities.

In a second step 200, indications from the patient concerning his/her perception of his/her own hearing with respect to one or more listening situations (which are then subject to specific audiometric tests) are received. Such second step is also advantageously carried out by the audiologist by recording data, through a software application, collected in the first meeting with the patient (or even in a second meeting, in any case before the delivery of the hearing aid). In particular, the second step 200 is aimed at determining the perception that the patient has of his/her own hearing in one or more different listening situations, optionally in a series of six different listening situations; advantageously, the software application graphically shows the collected data favouring a greater involvement of the patient as to awareness and measurement of the hearing impairments. By way of example and not by way of limitation, the different listening situations are six and comprise: hearing soft sounds; understanding words in quiet; understanding words in noise; situation of tolerable noise; capability to localise sounds; and ability of concentration during a dialogue. Optionally, the audiologist asks questions to the patient, using examples of daily life, possibly in line with the needs indicated in the first step 100; more optionally, for each listening situation, the patient gives an assessment of his/her own hearing according to a scale of integers from 0 to 10, wherein 0 corresponds to the perception of a total hearing loss (i.e. "I can not at all—subject of the question—") and 10 corresponds to the perception of absence of hearing loss (i.e. "I can perfectly—subject of the question—"). It must be noted that in other embodiments of the method according to the invention the scale may be a non-integer value scale the lower and upper limits of which can be even different from 0 and 10.

Thus memorised data allow to compare the hearing abilities perceived by the patient with the objective hearing abilities, detected in audiometric tests of subsequent steps of the method, in order to allow the patient, with the help of the audiologist, to choose the best hearing aid.

Figure 2:
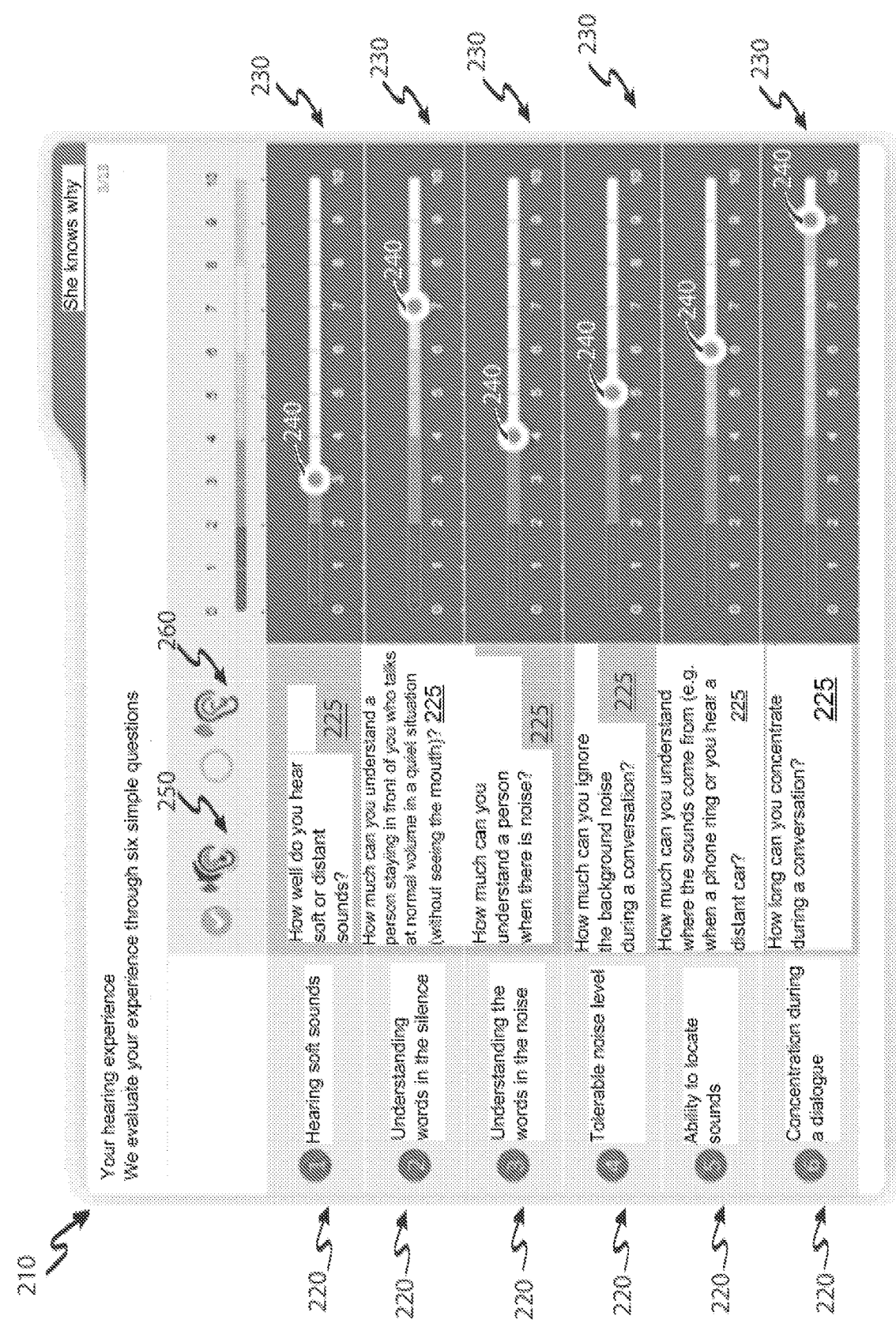
FIG. 2 shows a first graphic interface of a software application of which the method of FIG. 1 makes use.

Optionally, the software application comprises a coloured graphic interface on which, for each listening situation, the audiologist may move a cursor positioning it in correspondence of the value of the scale from 0 to 10 indicated by the patient, thus obtaining a graphic representation of the patient's indications which are memorised. FIG. 2 shows such a graphic interface 210 of the software application used in the preferred embodiment of the method according to the invention, wherein six listening situations 220 are visible, for each one of which a question (in a field 225), that the audiologist asks to the patient, and the related scale 230 of values from 0 to 10, along which the audiologist may move the cursor 240, are shown; also, the graphic interface 210 further shows two icons alternatively selectable to indicate whether the patient gives answers referred to an aided hearing that is after the application of the new hearing aid (icon 250—selected in FIG. 2) or to an unaided hearing (icon 260) that is before the application of the new hearing aid.

Still making reference to FIG. 1, then the method according to the invention comprises some steps, indicated with reference numerals 300 to 600 and which will be illustrated in detail later, wherein audiometric tests providing objective data relating to the listening situations determined in the second step 200 are performed.

Figure 3:
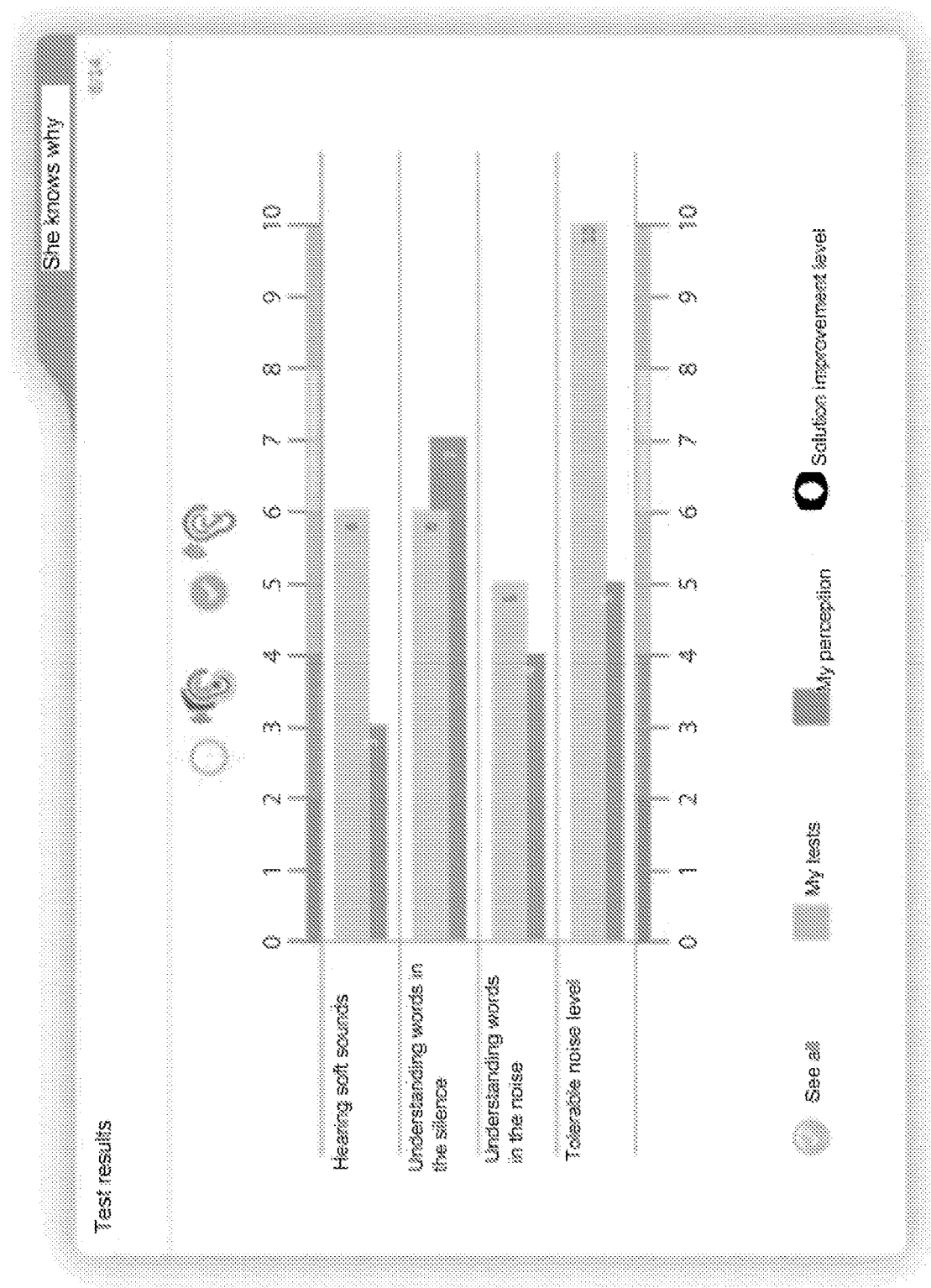
FIG. 3 shows a second graphic interface of the software application of which the method of FIG. 1 makes use.

The data collected in steps of audiometric tests are used in a subsequent seventh step 700 wherein the results of perceived and measured hearing are fused and shown, as shown in FIG. 3, giving to the patient a better comprehension and awareness of the situation of his/her own hearing, also graphically comparing the hearing ability that the person deems to have in the several listening situations with the results of the corresponding audiometric tests.

In an eighth step 800, the most suitable hearing aids are then determined, and in a ninth step 900 the related adjustment of the operating parameters, i.e. the settings of the electronic signal processing to perform, is automatically determined to allow to meet the needs determined in the first step 100. Advantageously, such eighth step 800 is made with the help of the software application that graphically displays the benefits obtainable by the patient with several hearing aid models, allowing the patient to make an informed choice of the specific hearing aid.

Steps performing the audiometric tests, carried out in the first meeting of the audiologist with the patient (or even in another meeting, in any case before the delivery of the hearing aid) are described in the following.

First of all, in a third step 300 a Pure Tone Audiometry, also known as PTA, test, described for instance in the UNI EN ISO 8253 standard and by M. Valente in "Pure-Tone Audiometry and Masking", Plural Press, 2009, i.e. an audiometric tone air and bone conduction test, and threshold of discomfort, is performed on the patient, wherein the patient wears a headset and hearing is not assisted by any hearing aid.

Afterwards, in a fourth step 400 an Acceptable Noise Level, also known as ANL, test, described for instance by A. K. Nabelek et al. in "Toleration of background noises: Relationship with patterns of hearing aid use by elderly persons", *Journal of Speech and Hearing Research*, 1991, 34, 679-685, i.e. a test of tolerance to noise, is performed on the patient, wherein the patient wears a headset when the test is performed outdoors, and the test is performed in free field (i.e. the patient does not wear any headset) when indoors (e.g. a laboratory or store), and hearing can be also assisted by a former hearing aid of which the patient already makes use (in particular, in the case where the indications on the subjective perception given in the second step 200 are given by a patient who already makes use of the former hearing aid, so as to have a significant comparison and useful information for the adjustment). The ANL test comprises one or more measurements, optionally five measurements.

In the case where the resulting value of the PTA test is not larger than 80 dB (i.e. PTA test value≤80 dB), the method then performs a fifth step 500 wherein a Speech in Noise, also known as SPIN, test, described for instance by J. L. Danhauer et al. in Handbook of Outcomes Measurement in Audiology, Singular Publishing Group, 2002, i.e. a test of understanding in noise, is performed, wherein the patient wears a headset when the test is performed outdoors, and the test is performed in free field (i.e. the patient does not wear any headset) when indoors (e.g. a laboratory or store), and hearing can be also assisted by a former hearing aid of which the patient already makes use (in particular, in the case where the indications on the subjective perception given in the second step 200 are given by a patient who already makes use of the former hearing aid, so as to have a significant comparison and useful information for the adjustment). In FIG. 1, branch 450 represents the check on the value of the PTA test that selects execution of the SPIN test or not.

In the case where the resulting value of the PTA test is larger than 80 dB (i.e. PTA test value>80 dB), or in the case where the resulting value of the PTA test is not larger than 80 dB (i.e. PTA test value 80 dB) and the resulting value of the SPIN test is larger than 6 (SPIN>6), the method performs a sixth step 600 wherein a Speech in Quiet, also known as SPIQ, test, also described for instance by J. L. Danhauer et al. in Handbook of Outcomes Measurement in Audiology, Singular Publishing Group, 2002, i.e. a test of understanding in quiet, is performed, wherein the patient wears a headset (when the test is performed both outdoors and indoors—e.g. a laboratory or store). In FIG. 1, branch 550 represents the check on the value of the SPIN that selects execution of the SPIQ test or not.

In the preferred embodiment, the four audiometric tests provide a result on a same specific measurement scale of integer values from 0 to 10. In particular, the method assigns value 10 to the value of the output of the audiometric test corresponding to person with normal hearing (i.e. the scale internationally recognised for each single audiometric test); such value decreases down to 0 with the increase of the hearing loss identified by the audiometric test. It must be noted that in other embodiments of the method according to the invention the specific measurement scale can be a non-integer value scale the lower and upper limits of which can be also different from 0 and 10; advantageously, the specific measurement scale is identical to the value scale used in the second step 200.

Tables 1-4 show the conversions between audiometric result of the four PTA, ANL, SPIN and SPIQ tests, respectively, and value (indicated with the term "score") assigned according to such unique specific measurement scale of the objective hearing situation of the patient:

TABLE 1

| PTA | |
|---|---|
| dB PTA | score |
| <20 | 10 |
| [20-25) | 9 |
| [25-30) | 8 |
| [30-35) | 7 |
| [35-40) | 6 |
| [40-50) | 5 |
| [50-59) | 4 |
| [60-70) | 3 |
| [70-80) | 2 |
| [80-90) | 1 |
| ≥90 | 0 |

TABLE 2

| ANL with Bubble Noise | |
|---|---|
| test result | score |
| 0 | 10 |
| 3 | 9 |
| 5 | 8 |
| 7 | 7 |
| 8 | 7 |
| 9 | 6 |
| 10 | 6 |
| 11 | 5 |
| 12 | 5 |
| 13 | 4 |
| 14 | 3 |

TABLE 2-continued

ANL with Bubble Noise

| test result | score |
|---|---|
| 15 | 2 |
| 16 | 1 |
| 25 | 0 |

TABLE 3

SPIN with SWN

| test result | score |
|---|---|
| −5 | 10 |
| −4 | 10 |
| −3 | 9 |
| −1 | 8 |
| 1 | 7 |
| 3 | 6 |
| 5 | 5 |
| 7 | 3 |
| 11 | 1 |
| 13 | 0 |
| 15 | 0 |
| 18 | 0 |
| 25 | 0 |

TABLE 4

SPIQ

| test result | score |
|---|---|
| 20 | 10 |
| 40 | 8 |
| 45 | 8 |
| 50 | 7 |
| 55 | 6 |
| 60 | 5 |
| 65 | 4 |
| 70 | 3 |
| 75 | 2 |
| 80 | 1 |
| 85 | 0 |
| 90 | 0 |
| 95 | 0 |
| 100 | 0 |
| 120 | 0 |

In this way, such unique specific scale permits to compare the values of the audiometric tests with the values of the perception of his/her own hearing by the patient determined in the second step 200, the data of which are already collected on the basis of a similar scale from 0 to 10. This further allows to determine the level of technology and performance necessary for the hearing aid.

In fact, the specific measurement scale on which the results of the four audiometric tests are provided gives indications to the audiologist for optimal adjustment of the hearing aid in a customised manner for the concerned patient. Advantageously, steps 300 to 600 are carried out by the audiologist by making use of a software application that allows data recording, optionally wherein a unique graphic interface collects and shows the results of all the audiometric tests, making them more comprehensible for the audiologist and the patient.

Figure 4:
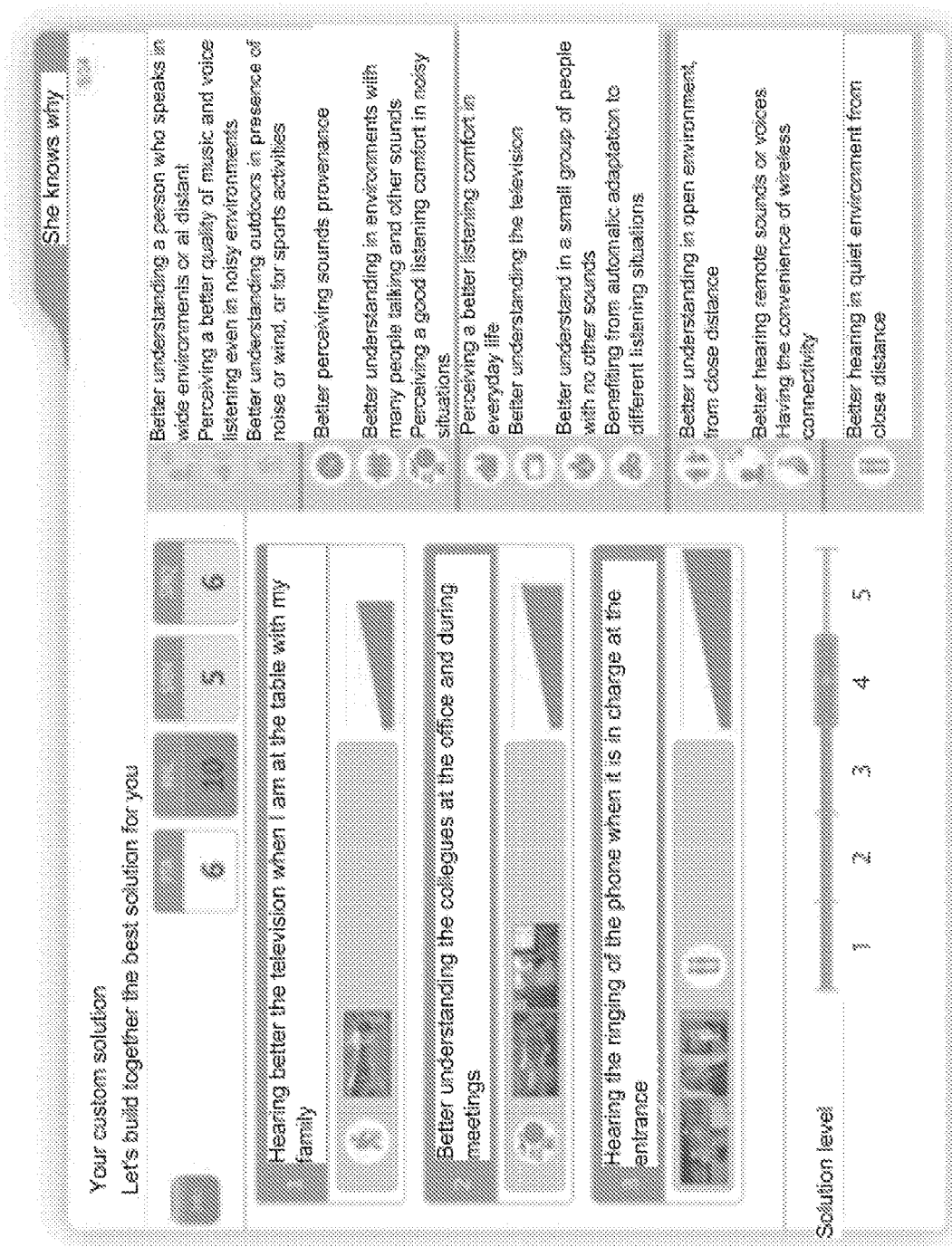
FIG. 4 shows a third graphic interface of the software application of which the method of FIG. 1 makes use.

Moreover, the software application allows to display (in eighth step 800 in FIG. 1) on a corresponding graphic interface, shown in FIG. 4, the benefits resulting from the different hearing aids available for the patient (and which he/she can choose), with particular reference to the needs recorded in the first step 100 of the method according to the invention. In this regard, the software application can optionally show an association between benefits and needs, thus highlighting the level of satisfaction of each need recorded in the first step 100 in relation to the type of hearing aid corresponding to a respective level of solution. By way of example, and not by way of limitation, FIG. 4 shows a graphic interface 310 that displays that to reach maximum satisfaction (indicated by a full green bar—as shown for the bar 320 of the need 3) for the need 1 is necessary a solution of level 5, while for the need 3 a level of solution 4 is sufficient. In this way, the software application renders graphically evident to the patient the level of satisfaction obtainable on the specific need (through the fill level of the green bar), on the basis of the type of solution chosen by the patient with the help of the audiologist.

As mentioned, the needs indicated by the patient in the second step 200 and the data obtained from the audiometric tests of audiometric test steps 300 to 600 on the unique measurement scale are used in an eighth step 800 in which one or more most suitable hearing aids are determined and in a ninth step 900 in which the related adjustment of the operating parameters, i.e. the settings of the electronic signal processing to carry out, is automatically determined. In particular, the functions of the electronic processing of the acoustic signal of each hearing aid of which the settings are adjusted comprise or consist of the following:

management of the amplification level, i.e. the gain for each frequency band;

with reference to amplitude compression, i.e. to gain variation inversely proportional to input signal level variation (whereby amplification reduces upon increase of the input signal and vice versa, so that the aid adds less amplification when there is less need for it because the sound stimulus is already sufficiently high):

management of level of intervention of compression, i.e. the level at which the aid stops amplifying in the same way all the signals (independently from their input level) and, instead, starts amplifying the input signals in a differentiated manner for each signal, applying a compression function, compression ratio, i.e. the ratio between input signal (only the part exceeding the level of intervention) and the output signal (from the compression function executed by the signal processing unit of the hearing aid) when compression is active;

management of the frequency compression and related frequency shift, i.e. the frequency shift that causes sound playing to occur at a frequency different from the original one;

microphone setting mode, so as to select the microphone operation mode (capable to simulate different hearing modes: front, rear, side) and to select the frequency band of the acquired signals;

with reference to the anti-feedback system selectively attenuating the frequencies at which the Larsen effect occurs (with the occurrence of a hiss from the hearing aid if the latter locks with the loudspeaker of the same aid), management of such anti-feedback system, i.e. the attenuation level at the frequencies at which the Larsen effect occurs;

Voice and Noise management (S/N Manager), i.e. the adjustment of attenuation and frequency of filters allowing to increase the Voice/Noise (Speech/Noise) ratio;

management of transient and sudden sounds, i.e. the adjustment of attenuation and frequency of filters eliminating transient and sudden sounds; and management of reverberant listening environments, i.e. management of microphone operation aimed at better capturing the main signal and excluding the one reflected by a reverberation environment.

As stated, the logic sequence of the audiometric tests is function of the result of a preceding audiometric test, with particular reference to the SPIN and SPIQ tests which may be alternative or even combined with each other. The software application of the preferred embodiment of the method according to the invention transforms the results of the three ANL, SPIN and SPIQ tests into one of three colours into which the values of such unique scale are transformed, so as to provide the audiologist with visual indications to adjust the several functions of the hearing aids available for the patient. In particular, the three colours correspond to the following settings (fittings) of the hearing aid: natural fitting, i.e. substantially no processing of the acoustic signal, optionally shown in green; from natural to moderately controlled fitting, i.e. with adjustments of specific operating parameters for the desired listening situation not larger than respective first modification thresholds, optionally shown in yellow; and from moderately controlled to significantly controlled fitting, i.e. with adjustments of specific operating parameters for the desired listening situation larger than the respective first modification thresholds, optionally shown in red.

By way of example, and not by way of limitation:

in case of natural fitting, the S/N manager parameters are set to a minimum, so as to limit as much as possible its operation, and the microphone management can simulate the natural hearing of the normal hearing ear, without introducing many changes upon variation of sound environment;

in case of fitting moderately controlled, the S/N manager parameters are set at a medium level, so as to intervene only if the noise level gets very high, and the microphone management can simulate the natural hearing of the normal hearing ear, and possibly carry out some correction in case of listening in difficult sound environments, with several sound sources not manageable by the S/N manager;

in case of significantly controlled fitting, the S/N manager parameters are set at a rather high level, so as to protect the patient from noises which he/she could perceive as troublesome, and the microphone management can vary the focusing (i.e. the direction of acquisition of acoustic signals) upon variation of the listening situations; also, an additional processing program with a different microphone mode with very narrow (i.e. directional) focusing can be manually managed by the patient.

Tables 5-7 show the conversions, automatically executed by the method in the ninth step 900, from the audiometric result to the values on the unique scale and from the latter to the respective fitting.

TABLE 5

ANL with Bubble Noise

| test result | score | Fitting |
|---|---|---|
| 0 | 10 | Natural |
| 3 | 9 | |
| 5 | 8 | From natural to |
| 7 | 7 | moderately |
| 8 | 7 | controlled fitting |
| 9 | 6 | |
| 10 | 6 | From moderately |
| 11 | 5 | controlled to |
| 12 | 5 | significantly |
| 13 | 4 | controlled fitting |
| 14 | 3 | |
| 15 | 2 | |
| 16 | 1 | |
| 25 | 0 | |

TABLE 6

SPIN with SWN

| test result | score | Fitting |
|---|---|---|
| −5 | 10 | Natural |
| −4 | 10 | |
| −3 | 9 | From natural to |
| −1 | 8 | moderately |
| 1 | 7 | controlled fitting |
| 3 | 6 | |
| 5 | 5 | |
| 7 | 3 | From moderately |
| 11 | 1 | controlled to |
| 13 | 0 | significantly |
| 15 | 0 | controlled fitting |
| 18 | 0 | |
| 25 | 0 | |

TABLE 7

| SPIQ test result | Score | Fitting |
|---|---|---|
| 20 | 10 | From natural to |
| 40 | 8 | moderately |
| 45 | 8 | controlled |
| 50 | 7 | fitting |
| 55 | 6 | |
| 60 | 5 | |
| 65 | 4 | From moderately |
| 70 | 3 | controlled to |
| 75 | 2 | significantly |
| 80 | 1 | controlled fitting |
| 85 | 0 | |
| 90 | 0 | |
| 95 | 0 | |
| 100 | 0 | |
| 120 | 0 | |

By way of example, and not by way of limitation, Tables 8-10 (which can be optionally lookup tables automatically read by the software application implementing the method according to the invention) show the indications of the fitting parameters for microphones and algorithms that the software application of the preferred embodiment of the method according to the invention automatically provides to the audiologist in step 900 to adjust the operating parameters (i.e. the several functions) of each one of the available hearing aids selected in step 800 to allow meeting the needs determined in step 100, in case of some aids from Siemens® (Table 8), some aids from Beltone® (Table 9) and some aids from Phonak® (Table 10).

TABLE 8

Hearing aids from Siemens ®: 7bx, 5bx, 3bx, Orion, Sirion

| | | |
|---|---|---|
| Natural fitting | Microphones | Products 7bx, 5bx, 3bx: True Ear<br>Orion: set "Automatic" directionality by flagging Speech only in noise and "low" low directivity Level.<br>Sirion: since there is no microphone similar to human ear products from Sirion are not the best choice for a natural fitting. If necessary, use "Static Directional" |
| | Algorithms | Adjustment of Voice and Noise: OFF or to a minimum<br>Soundsmoothing: OFF or to a minimum<br>Frequency compression: OFF or to a minimum<br>Feedback cancellation: ON |
| From natural to moderately controlled fitting | Microphones | Products 7bx, 5bx, 3bx: True Ear<br>Orion: set "Automatic" directionality by flagging Speech only in noise and "standard" low directivity Level.<br>Sirion: products from Sirion are not the best choice for a fitting from natural to moderately controlled.<br>If necessary, use "Static Directional" |
| | Algorithms | Adjustment of Voice and Noise: setting from minimum to medium<br>Soundsmoothing: setting from minimum to medium<br>Frequency compression: OFF<br>Feedback cancellation: ON |
| From moderately controlled to significantly controlled fitting | Microphones | Products 7bx, 5bx, 3bx: True Ear and its functions depending on the customer's needs<br>Orion: set "Automatic" and add a program with directional microphone<br>Sirion: set "Automatic" and add a program with directional microphone |
| | Algorithms | Adjustment of Voice and Noise: setting from medium to maximum<br>Soundsmoothing: setting from medium to maximum<br>Frequency compression: OFF<br>Feedback cancellation: ON |

TABLE 9

Hearing aids from Beltone ®: Legend 17, Legend 9, Legend 6, First 6, Origin 3, Origin 2

| | | |
|---|---|---|
| Natural fitting | Microphones | Legend 17: setting "Natural listening" directionality<br>Legend 9: since there is no microphone similar to human ear these products are not the best choice for a natural fitting. If necessary, use "Speech Spotter Pro" with "Large" Directional Beam Width<br>Legend 6: since there is no microphone similar to human ear these products are not the best choice for a natural fitting. If necessary, use "Speech Spotter Pro Basic"<br>First 6: set "Adaptive Directionality" directionality<br>Origin 3 and Origin 2: since there is no microphone similar to human ear these products are not the best choice for a natural fitting. If necessary, use "Adaptive Directionality" (different from the one of First 6 because there is no Band Split Directionality function) |
| | Algorithms | Expansion: OFF<br>Sound Cleaner Pro: OFF or to a minimum<br>Soundshifter: OFF<br>Gain optimizer: similar in all the environments<br>Feedback Eraser: ON |
| From natural to moderately controlled fitting | Microphones | Legend 17 and Legend 9: set "Speech Spotter Pro" directionality with "Large" Directional Beam Width<br>Legend 6 and First 6: set "Speech Spotter Basic" directionality<br>Origin 3: set "Speech Spotter Basic" directionality. Functionality lower than the one in Legend 6 and First 6 because there is no Band Split Directionality function<br>Origin 2: set "Adaptive Directionality" directionality |
| | Algorithms | Expansion: OFF<br>Sound Cleaner Pro: from medium to moderate<br>Soundshifter: OFF<br>Gain optimizer: use default settings<br>Feedback Eraser: ON |
| From moderately controlled to significantly controlled fitting | Microphones | Legend 17: set "Directionality Crosslink with Natural listening" directionality<br>Legend 9: set "Directionality Cross Link" directionality<br>Legend 6 and First 6: since there is no microphone with high performance directionality these products are not the best choice for a fitting from moderately controlled to significantly controlled fitting. If necessary, use "Speech Spotter Basic".<br>Origin 3: since there is no microphone with high performance directionality these products are not the best choice for a fitting from moderately controlled to significantly controlled fitting. If necessary, use "Speech Spotter Basic". Functionality lower than the one in Legend 6 and First 6 because there is no Band Split Directionality function<br>Origin 2: since there is no microphone with high performance directionality these products are not the best choice for a fitting from moderately controlled to significantly controlled fitting. If necessary, use "Adaptive Directionality" |
| | Algorithms | Expansion: medium or moderate<br>Sound Cleaner Pro: from moderate to maximum<br>Soundshifter: OFF<br>Gain optimizer: use depending on the customer's needs<br>Feedback Eraser: ON |

TABLE 10

Hearing aids from Phonak ®: Products 90, 70, 50

| | | |
|---|---|---|
| Natural fitting | Microphones | Products 90 and 70: set Real Ear Sound<br>Products 50: since there is no microphone similar to human ear these products are not the best choice for a natural fitting. If necessary, use "Fixed Directional" |
| | Algorithms | Noiseblock: OFF or to a minimum<br>AutoSense: OFF, select Situation in quiet as $1^{st}$ program<br>SoundRecover: OFF<br>Echo Block: OFF<br>WindBlock: ON or OFF depending on the customer's needs<br>WhistleBlock: ON |
| From natural to moderately controlled fitting | Microphones | Products 90 and 70: set Real Ear Sound<br>Products 50: use microphone proposed as default |
| | Algorithms | Noiseblock: from minimum to medium values<br>AutoSense: ON with slow transition speed<br>SoundRecover: OFF<br>Echo Block: OFF<br>WindBlock: ON or OFF depending on the customer's needs<br>WhistleBlock: ON |

TABLE 10-continued

Hearing aids from Phonak ®: Products 90, 70, 50

| From moderately controlled to significantly controlled fitting | Microphones | Products 90 and 70: set Real Ear Sound<br>Products 50: use microphone proposed as default and add a program with directional microphone |
| --- | --- | --- |
| | Algorithms | Noiseblock: from medium to high values<br>AutoSense: ON with fast transition speed<br>SoundRecover: OFF<br>EchoBlock: ON<br>WindBlock: ON or OFF depending on the customer's needs<br>WhistleBlock: ON |

Optionally, the method for adjusting in a customised manner a hearing aid according to the invention may comprise an additional step for checking the adjustment effectiveness that comprises executing the SPIN and SPIQ tests, illustrated above, with the hearing aid applied to the patient. In particular, in the additional checking step the SPIN test is performed if the fifth step 500 has been executed (i.e. if the SPIN test had been already performed) and the SPIQ test is performed if the sixth step 600 has been executed (i.e. if the SPIQ test had been already performed) and if it is performed within a structure equipped with free field (e.g. in a laboratory or store). In case of the SPIN test, the competing noise for the first word is anticipated by 10 seconds before the same word, to permit the S/N and microphone algorithms performed by the processing unit to stabilise and render their intervention effective. Furthermore, in such additional checking step a balancing test within a structure equipped with free field (e.g. in a laboratory or store) may be also optionally performed to tune the correct balance between the two ears for a better hearing.

Figure 5:
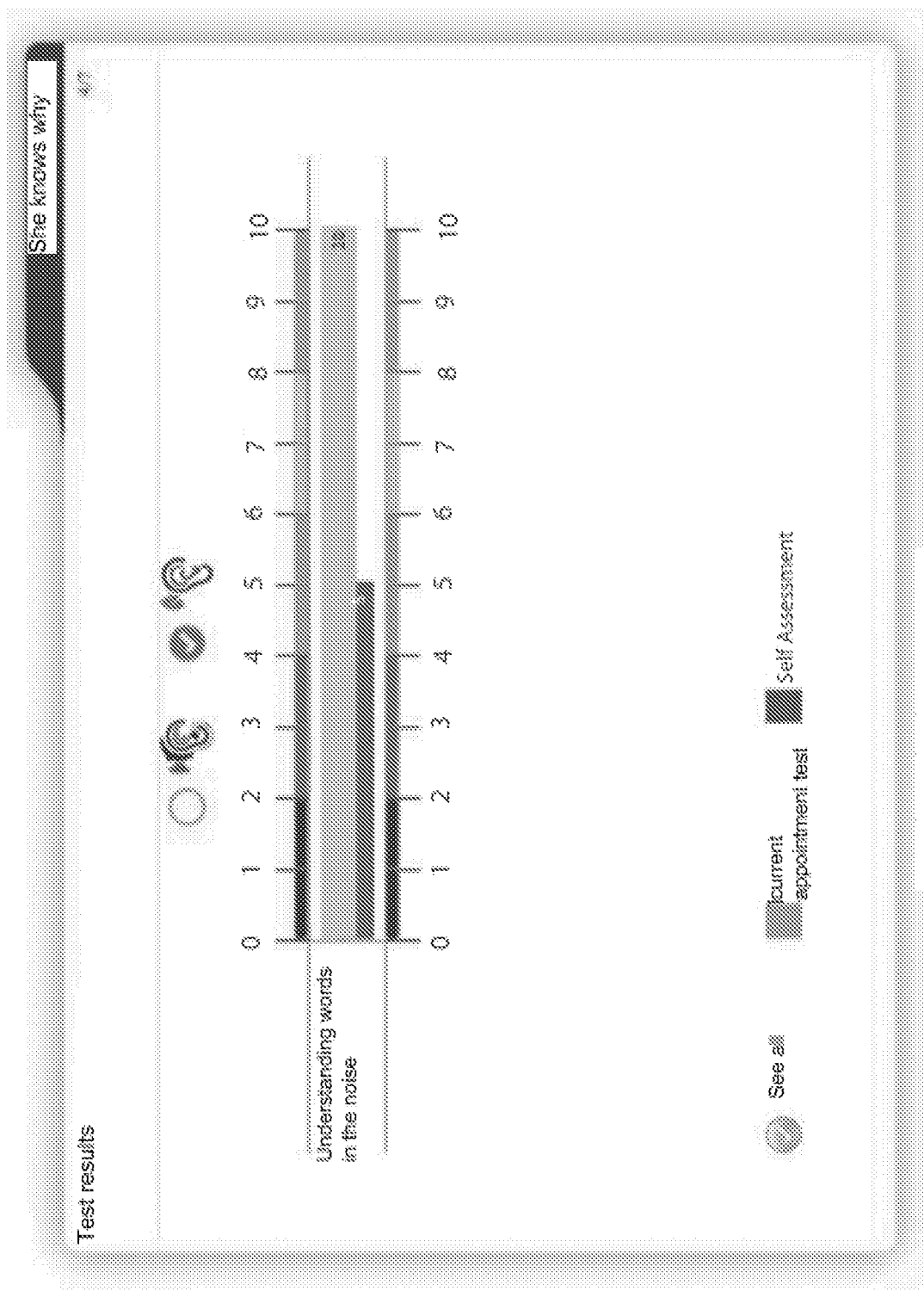
FIG. 5 shows a fourth graphic interface of the software application of which the method of FIG. 1 makes use.

In such case, the method optionally allows to show a comparison of the hearing abilities perceived by the patient with the objective hearing abilities detected in the audiometric tests, highlighting with data of the (pre- and post-application) tests the benefits resulting from the application of the hearing aid. In particular, the software application of which the preferred embodiment of the method according to the invention makes use shows such comparison in a suitable graphic interface shown in FIG. 5.

Furthermore, the method for selecting and adjusting in a customised manner a hearing aid according to the invention may further optionally comprise a final or iterative checking step after a time period of use of the aid (e.g., for the first check, after 15 days, and for the successive checks after 12 months), in which patient's indications on achievement of goals (i.e. meeting of the needs) and check of the progressive increase of satisfaction are received and recorded, similarly to the second step 200, and audiometric tests to control fitting are then carried out, again executing, if necessary, the SPIN and SPIQ tests (if the fifth step 500 and sixth step 600, respectively, have been already executed). Even in this case, the preferred embodiment of the method can make use of the software application allowing to display the achieved goals.

The preferred embodiments of this invention have been described and a number of variations have been suggested hereinbefore, but it should be understood that those skilled in the art can make other variations and changes without so departing from the scope of protection thereof, as defined by the attached claims.

The invention claimed is:

1. Method for selecting and adjusting in a customised manner a hearing aid, including a signal processing unit configured to process an electrical signal coming from one or more microphones and to play a resulting processed electrical signal in an ear canal of a patient through a miniature loudspeaker, wherein processing of the electrical signal is adjustable by means of settings of one or more operating parameters of the signal processing unit, wherein the method comprises the following steps:

A. receiving indications on one or more needs of a patient;
B. receiving indications from the patient concerning his/her perception of his/her own hearing with respect to one or more listening situations by assigning a respective value on a first value scale having a lower limit and an upper limit;
C. performing a Pure Tone Audiometry audiometric test, also known as PTA test, on the patient, wherein the patient wears a headset and hearing is not assisted by any hearing aid;
D. performing an Acceptable Noise Level audiometric test, also known as ANL test, on the patient;
E. in the case where the resulting value of the audiometric PTA test is not larger than 80 dB, performing a Speech in Noise test, also known as SPIN test, on the patient;
F. in the case where the resulting value of the audiometric PTA test is larger than 80 dB, or in the case where the resulting value of the audiometric PTA test is not larger than 80 dB and the resulting value of the SPIN test is larger than 6, performing a Speech in Quiet test, also known as SPIQ test, on the patient, wherein the patient wears a headset;
G. displaying the resulting values of the audiometric tests performed in steps C, D, E and/or F on a same second value scale;
H. on the basis of said one or more needs of the patient on which indications have been received in step A and on the basis of the resulting values of all the audiometric tests which have been performed in steps C and D and E and F, selecting one or more available hearing aids,
J. for each one of said one or more available hearing aids selected in step H, on the basis of said one or more needs of the patient on which indications have been received in step A and on the basis of the resulting values of all the audiometric tests which have been performed in steps C and D and E and F, automatically determining a related adjustment of operating parameters of the respective signal processing unit to allow meeting the needs determined in step A.

2. Method according to claim 1, wherein in step D and step E the patient wears a headset when the ANL and SPIN tests, respectively, are performed outdoors, while the ANL and SPIN tests, respectively, are performed in free field when indoors.

3. Method according to claim 1, wherein the ANL test of step D comprises one or more measurements.

4. Method according to claim 1, wherein said first value scale is a scale of integers from 0 to 10, wherein 0 corresponds to a perception of total hearing loss and 10 corresponds to a perception of absence of hearing loss.

5. Method according to claim 1, wherein said second value scale is identical to said first value scale.

6. Method according to claim 1, wherein said operating parameters concern functions of electronic processing of the acoustic signal comprising or consisting of:

a management of amplification level;
with reference to an amplitude compression, a management of level of intervention of compression and a compression ratio;

a management of a frequency compression and of a related frequency shift;

a microphone setting mode for selecting one or both of two microphone inputs corresponding to the front microphone and the rear microphone and for selecting a frequency band of the signals acquired by the selected microphone or microphones;

a management of an anti-feedback system configured to selectively attenuate frequencies at which a Larsen effect occurs;

a Voice and Noise management (S/N Manager);

a management of transient and sudden sounds; and a management of reverberant listening environments.

7. Method according to claim 1, wherein said adjustment of operating parameters in step J comprises transforming the results of the ANL, SPIN and/or SPIQ tests of steps D, and E and/or F, respectively, in one of the following three settings:

natural fitting that substantially entails no processing of the acoustic signal;

from natural to moderately controlled fitting that entails adjustments of specific operating parameters for at least one desired listening situation not larger than respective first modification thresholds; and from moderately controlled to significantly controlled fitting that entails adjustments of specific operating parameters for at least one desired listening situation larger than the respective first modification thresholds.

8. Method according to claim 1, wherein said one or more needs on which indications are received in step A are selected from the group comprising: better hearing in quiet environment from close distance; better understanding in open environment from close distance; better hearing distant sounds or voices; better comfort in daily listening; better understanding a television; better understanding in a small group of people with no other sounds; automatic adaptation to different listening situations; wireless connectivity; better perceiving a sound provenance; better understanding in environment with many people talking and other sounds; good listening comfort in noisy situations; better understanding a person speaking in wide environment or at a distance; better quality of listening to music and voice even in presence of noise; better understanding outdoors in presence of noise or wind and/or for sports activities.

9. Method according to claim 1, wherein said one or more listening situations with respect to which indications from the patient concerning his/her perception of his/her own hearing are received in step A are six different hearing situations comprising: hearing soft sounds; understanding words in quiet; understanding words in noise; situation of tolerable noise; ability to locate sounds; and ability of concentration during a dialogue.

10. Method according to claim 1, further comprising an additional checking step that includes performing a SPIN test, if step E has been performed, and performing a SPIQ test, if step F has been performed, with the hearing aid adjusted according to the related adjustment of operating parameters of the respective signal processing unit determined in step J.

11. Method according to claim 10, wherein in the SPIN test of the additional checking step patient's hearing is aided by a former hearing aid.

12. Method according to claim 10, wherein said additional checking step further includes performing a balancing test within a structure equipped with free field.

13. Method according to claim 1, wherein the method steps are performed by means of a software application.

14. Method according to claim 13, wherein step G displays a comparison of hearing abilities perceived by the patient with objective hearing abilities detected in the audiometric tests performed in steps C, D, E and/or F.

15. Method according to claim 13, wherein step H displays benefits resulting from different hearing aids available for the patient with reference to said one or more needs on which indications have been received in step A.

16. Method according to claim 1, wherein the ANL test of step D comprises five measurements.

17. Method according to claim 1, wherein said adjustment of operating parameters in step J comprises transforming the results of the ANL, SPIN and/or SPIQ tests of steps D, and E and/or F, respectively, in one of the following three settings:

natural fitting that substantially entails no processing of the acoustic signal, wherein the S/N manager parameters are set to a minimum for limiting its operation as much as possible and microphone management can simulate a natural listening of a normal hearing ear substantially without introducing changes upon variation of sound environment;

from natural to moderately controlled fitting that entails adjustments of specific operating parameters for at least one desired listening situation not larger than respective first modification thresholds, wherein the S/N manager parameters are set at a medium level to intervene only if a noise level gets higher than a respective noise threshold and the microphone management can simulate a natural listening of a normal hearing ear; and from moderately controlled to significantly controlled fitting that entails adjustments of specific operating parameters for at least one desired listening situation larger than the respective first modification thresholds, wherein the S/N manager parameters are set at a high level to protect the patient from noises which he/she could perceive as troublesome and the microphone management can vary focusing upon variation of listening situation.

18. Method according to claim 1, wherein said adjustment of operating parameters in step J comprises transforming the results of the ANL, SPIN and/or SPIQ tests of steps D, and E and/or F, respectively, in one of the following three settings:

natural fitting that substantially entails no processing of the acoustic signal, wherein the S/N manager parameters are set to a minimum for limiting its operation as much as possible and microphone management can simulate a natural listening of a normal hearing ear substantially without introducing changes upon variation of sound environment;

from natural to moderately controlled fitting that entails adjustments of specific operating parameters for at least one desired listening situation not larger than respective first modification thresholds, wherein the S/N manager parameters are set at a medium level to intervene only if a noise level gets higher than a respective noise threshold and the microphone management can simulate a natural listening of a normal hearing ear, and it can carry out one or more corrections in case of listening in sound environments with several sound sources not manageable by the S/N manager; and from moderately controlled to significantly controlled fitting that entails adjustments of specific operating parameters for at least one desired listening situation larger than the respective first modification thresholds, wherein the S/N manager parameters are set at a high level to protect the patient from noises which he/she could perceive as troublesome and the microphone management can vary focusing upon variation of listening situation.

* * * * *